(12) United States Patent
Doria et al.

(10) Patent No.: US 8,080,374 B2
(45) Date of Patent: Dec. 20, 2011

(54) METHODS OF DIAGNOSING CARDIOVASCULAR DISEASE

(75) Inventors: Alessandro Doria, Cambridge, MA (US); Xiaowei Ma, Beijing (CN)

(73) Assignee: Joslin Diabetes Center, Inc., Boston, MA (US)

(*) Notice: Subject to any disclaimer, the term of this patent is extended or adjusted under 35 U.S.C. 154(b) by 634 days.

(21) Appl. No.: 11/248,578

(22) Filed: Oct. 12, 2005

(65) Prior Publication Data

US 2006/0147953 A1 Jul. 6, 2006

Related U.S. Application Data

(63) Continuation-in-part of application No. PCT/US2005/016370, filed on May 10, 2005.

(60) Provisional application No. 60/569,898, filed on May 11, 2004.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6.1; 435/91.1; 435/91.2; 536/24.3

(58) Field of Classification Search .................. None
See application file for complete search history.

(56) References Cited

U.S. PATENT DOCUMENTS 6,322,976 B1 * 11/2001 Aitman et al. ............... 435/6

OTHER PUBLICATIONS rs1984112; dbSNP; National Library of Medicine, Jan. 2001.*
Hanawa et al; J. Med. Genet. vol. 39, pp. 286-291, 2002.*
rs1761667 (dbSNP; Nov. 2000).*
Ma et al; Human Molecular Genetics, vol. 13, 2004, pp. 2197-2205.*
(ss3324602, dbSNP build 110, Oct. 2001.*
International Search Report and Written Opinion for International Application No. PCT/US05/16370, 14 pages (Feb. 17, 2006).
Hanawa et al., "Identification of cryptic splice site, exon skipping, and novel point mutations in type I CD36 deficiency," J. Med. Genet., 39:286-291 (2002).
Ma et al., "A common haplotype at the CD36 locus is associated with high free fatty acid levels and increased cardiovascular risk in Caucasians," Human Molecular Genetics, 13(19):2197-2205 (2004).
Tanaka et al., "Defect in human myocardial long-chain fatty acid uptake is caused by FAT/CD36 mutations," J. Lipid Res., 42:751-759 (2001).
Abumrad et al., "Cloning of a rat adipocyte membrane protein implicated in binding or transport of long-chain fatty acids that is induced during preadipocyte differentiation. Homology with human CD36," J. Biol. Chem., 268:17665-17668, (1993).
Aitman et al., "Identification of Cd36 (Fat) as an insulin-resistance gene causing defective fatty acid and glucose metabolism in hypertensive rats," Nat. Genet., 21:76-83, (1999).
Chen et al., "Troglitazone inhibits atherosclerosis in apolipoprotein E-knockout mice: pleiotropic effects on CD36 expression and HDL," Arterioscler. Thromb. Vasc. Biol., 21:372-7 (2001).
Endemann, et al., "CD36 is a receptor for oxidized low density lipoprotein," J. Biol. Chem., 268:11811-11816, (1993).
Febbraio, et al., "A null mutation in murine CD36 reveals an important role in fatty acid and lipoprotein metabolism," J. Biol. Chem., 274:19055-19062, (1999).
Febbraio et al., "CD36: a class B scavenger receptor involved in angiogenesis, atherosclerosis, inflammation, and lipid metabolism," J. Clin. Invest., 108:785-791, (2001).
Furuhashi et al., "Insulin sensitivity and lipid metabolism in human CD36 deficiency," Diabetes Care, 26:471-474, (2003).
Goudriaan et al., "CD36 deficiency increases insulin sensitivity in muscle, but induces insulin resistance in the liver in mice," J. Lipid. Res., 44:2270-2277, (2003).
Greenwalt et al., "Membrane glycoprotein CD36: a review of its roles in adherence, signal transduction, and transfusion medicine," Blood, 80:1105-1115, (1992).
Hajri et al., "Defective fatty acid uptake modulates insulin responsiveness and metabolic responses to diet in CD36-null mice," J. Clin. Invest., 109:1381-1389, (2002).
Hirano et al., "Pathophysiology of human genetic CD36 deficiency," Trends Cardiovasc. Med., 13:136-41, (2003).
Ibrahimi et al., "Expression of the CD36 homolog (FAT) in fibroblast cells: effects on fatty acid transport," Proc. Natl. Acad. Sci. U. S. A., 93:2646-2651, (1996).
Kajihara et al., "Association of the Pro90Ser CD36 mutation with elevated free fatty acid concentrations but not with insulin resistance syndrome in Japanese," Clin. Chim. Acta., 314:125-130, (2001).
Kashiwagi et al., "Molecular basis of CD36 deficiency. Evidence that a 478C→T substitution (proline90→serine) in CD36 cDNA accounts for CD36 deficiency," J. Clin. Invest., 95:1040-1046, (1995).
Kuniyasu et al., "CD36-mediated endocytic uptake of advanced glycation end products (AGE) in mouse 3T3-L1 and human subcutaneous adipocytes," FEBS Letters, 537:85-90, (2003).
Laws et al., "Differences in insulin suppression of free fatty acid levels by gender and glucose tolerance status. Relation to plasma triglyceride and apolipoprotein B concentrations," Insulin Resistance Atherosclerosis Study (IRAS) Investigators. Arteriosclerosis, Thrombosis, and Vascular Biology, 17:64-71, (1997).
Lewis et al., "Disordered fat storage and mobilization in the pathogenesis of insulin resistance and type 2 diabetes," Endocr. Rev., 23:201-229, (2002).
Miyaoka et al., "CD36 deficiency associated with insulin resistance," Lancet, 357:686-687, (2001).
Pravenec et al., "Transgenic rescue of defective Cd36 ameliorates insulin resistance in spontaneously hypertensive rats," Nat. Genet., 27:156-158, (2001).
Qi, et al, "Pharmacogenetic evidence that cd36 is a key determinant of the metabolic effects of pioglitazone," J. Biol. Chem., 277:48501-48507, (2002).
Ruiz-Velasco et al., "Statins upregulate CD36 expression in human monocytes, an effect strengthened when combined with PPAR-gamma ligands Putative contribution of Rho GTPases in station-induced CD36 expression," Biochem. Pharmacol, 67:303-13 (2004).

(Continued)

*Primary Examiner* — Jehanne Sitton
(74) *Attorney, Agent, or Firm* — Pierce Atwood LLP; Joseph M. Maraia; Isabelle M. Clauss

(57) ABSTRACT

Described herein are methods for diagnosing increased risk of cardiovascular disease in a subject, based on the presence or absence of polymorphisms in the D36 gene.

12 Claims, 3 Drawing Sheets

OTHER PUBLICATIONS

Sato et al., "Dual promoter structure of mouse and human fatty acid translocase/CD36 genes and unique transcriptional activation by peroxisome proliferator-activated receptor alpha and gamma ligands," J. Biol. Chem., 277, 15703-15711, (2002).

Stahlberg et al., "Female-predominant expression of fatty acid translocase/CD36 in rat and human liver," Endocrinology, 145:1972-1979 (2004).

Steinberg, "Low density lipoprotein oxidation and its pathobiological significance," J. Biol. Chem., 272:20963-20966, (1997).

Tandon et al., "Identification of glycoprotein IV (CD36) as a primary receptor for platelet-collagen adhesion," J. Biol. Chem., 264:7576-7583, (1989).

Tontonoz et al., "PPARgamma promotes monocyte/macrophage differentiation and uptake of oxidized LDL," Cell, 93, 241-252, (1998).

Warram et al., "Epidemiology of non-insulin-dependent diabetes mellitus and its macrovascular complications. A basis for the development of cost-effective programs," Endocrinol. Metab. Clin. North Am., 26:165-88, (1997).

\* cited by examiner

| refSNP ID | Position† | Variation | Frequency‡ | Location¶ |
|---|---|---|---|---|
| rs1984112 | -33137 | A>G | 0.32 | 5'flanking exon 1A |
| rs1761667 | -31118 | A>G | 0.45 | 5'flanking exon 1A |
| rs1360741 | -28927 | A>G | 0.11 | 5'flanking exon 1A |
|  | -22674 | T>C |  |  |
| rs2366855 | -22602 | A>T | 0.45 | Exon 1A |
| rs1537593 | -22146 | T>C | 0.90 | Intron 1A / 5' flanking exon 1B |
| rs1953298 | -10606 | T>C | 0.55 | Intron 1A / 5' flanking exon 1B |
| rs1953299 | -10432 | G>T | 0.47 | Intron 1A / 5' flanking exon 1B |
| rs1334512 | -8153 | G>T | 0.32 | Intron 1A / 5' flanking exon 1B |
| rs1534314 | -4949 | G>A | 0.08 | Intron 1B |
| rs1527479 | -3489 | T>C | 0.55 | Intron 1B |
| rs1049654 | -602 | A>C | 0.54 | Exon 2A (5'UTR) |
| rs3211821§ | 2507 | A>G | 0.44 | Intron 3 |
| rs997906§ | 3779 | A>T | 0.37 | Intron 3 |
| rs3211873§ | 11555 | C>T | 0.08 | Intron 4 |
| rs1924§ | 15342 | G>A | 0.07 | Intron 5 |
| rs3211915§ | 18673 | Del 29 bp | 0.46 | Intron 7 |
| rs3211928§ | 21664 | G>C | 0.46 | Intron 8 |
| rs1527483§ | 25444 | G>A | 0.12 | Intron 11 |
| rs3840546§ | 27645 | Del 16 bp | 0.13 | Exon14 (3'UTR) |
| rs7755 | 30215 | G>A | 0.49 | Exon 15 (3'UTR) |
| rs1049673 | 30294 | C>G | 0.48 | Exon 15 (3'UTR) |

FIG. 1

| | Haplotype | -33137A>G | -31118A>G | 25443G>A | 27664del | 30293C>G | Frequency | Score | p | Global p |
|---|---|---|---|---|---|---|---|---|---|---|
| Block 1 | 1 | G | G | - | - | - | 0.452 | -2.780 | 0.007 | |
| | 2 | A | G | - | - | - | 0.099 | -0.156 | 0.890 | |
| | 3 | A | A | - | - | - | 0.430 | 2.840 | 0.005 | 0.031 |
| Block 2 | 1 | - | - | G | I | G | 0.418 | -3.050 | 0.002 | |
| | 2 | - | - | G | D | C | 0.080 | 1.269 | 0.212 | |
| | 3 | - | - | G | I | C | 0.448 | 1.941 | 0.044 | 0.020 |
| Block 1+2 | 1 | G | G | G | I | G | 0.312 | -2.297 | 0.023 | |
| | 2 | G | G | G | I | C | 0.114 | -1.555 | 0.140 | |
| | 3 | A | A | G | I | G | 0.061 | -1.216 | 0.220 | |
| | 4 | A | A | G | D | C | 0.054 | 1.250 | 0.210 | |
| | 5 | A | A | G | I | C | 0.304 | 3.001 | 0.001 | 0.020 |
FIG. 3
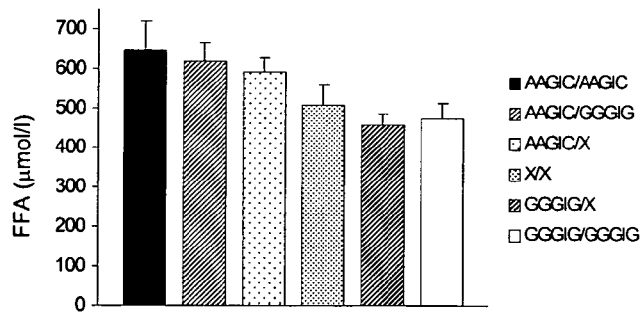
FIG. 4A
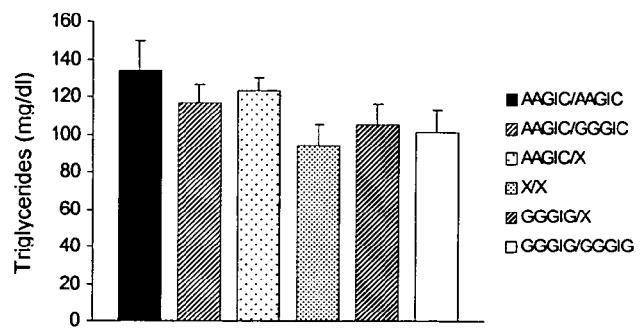
FIG. 4B

METHODS OF DIAGNOSING CARDIOVASCULAR DISEASE

CLAIM OF PRIORITY

This application is a continuation in part of International Patent Application No. PCT/US2005/016370, filed May 10, 2005, and claims the benefit under 35 USC §119(e) to U.S. Provisional Patent Application Ser. No. 60/569,898, filed on May 11, 2004, the entire contents of which are hereby incorporated by reference.

GOVERNMENT SUPPORT

The work described herein was carried out, at least in part, using funds from the U.S. government under grants HL73168, DK60837, and DK36836 awarded by the National Institutes of Health. The government has certain rights in the invention.

BACKGROUND

CD36, also known as platelet glycoprotein IV or IIIb, is an 88 kDa membrane protein expressed on the surface of a wide variety of cell types, including adipocytes, skeletal muscle cells, platelets, endothelial cells, and monocytes/macrophages (Febbraio et al., J. Clin. Invest., 108:785-91 (2001)). Initially identified for its binding to collagen and thrombospondin (TSP-1) in platelets, CD36 is a class B scavenger receptor recognizing a variety of ligands including long-chain fatty acids, modified LDL, anionic phospholipids, *Plasmodium falciparum*-infected erythrocytes, and apoptotic cells (Febbraio et al., J. Clin. Invest., 108:785-91 (2001); Abumrad et al., J. Biol. Chem., 268:17665-8 (1993); Tandon et al., J. Biol. Chem., 264:7576-83 (1989); Greenwalt et al., Blood, 80:1105-15 (1992)).

Several recent findings suggest a role for CD36 as an important regulator of the metabolic pathways involved in insulin-resistance. CD36 facilitates the membrane transport of long-chain fatty acids (FA) into muscle and adipose tissues (Ibrahimi et al., Proc. Natl. Acad. Sci. USA, 93:2646-51 (1996)). Increased FA availability can induce insulin resistance if the capacity of adipose tissue to store triglycerides and/or that of muscle to oxidize FA is exceeded (Lewis et al., Endocr. Rev., 23:201-29 (2002)). As a result, alterations in CD36 level may be involved in the development of diet-induced insulin-resistance, as suggested by findings in rodents (Hajri et al., J. Clin. Invest., 109:1381-9 (2002)). Homozygous disruption of the CD36 locus in mice leads to hepatic insulin-resistance with high plasma free fatty acids and triglycerides (Febbraio et al., J. Biol. Chem., 274:19055-62 (1999); Goudriaan et al., J. Lipid. Res., 44:2270-7 (2003)). Transgenic rescue of CD36 in the spontaneously hypertensive rat (SHR) strain, in which the CD36 gene is severely mutated, ameliorates the metabolic syndrome typical of this animal model (Aitman et al., Nat. Genet., 21:76-83 (1999); Pravenec et al., Nat. Genet., 27:156-8 (2001)). Furthermore, CD36 is regulated by the peroxisome proliferator activated receptor gamma (PPARγ) and is a gene target of thiazolidinediones (TZDs), agonists of this nuclear receptor (Tontonoz et al., Cell, 93:241-52 (1998)). Up-regulation of adipocyte or muscle CD36 by TZDs appears to mediate some of the insulin sensitizing effects of these drugs (Qi et al., J. Biol. Chem., 277:48501-7 (2002)).

SUMMARY OF THE INVENTION

The invention is based, in part, on the inventors' discovery that certain polymorphisms and/or haplotypes within the CD36 gene correlate with increased risk of cardiovascular disease.

Accordingly, in one aspect, the invention features methods for evaluating a subject, e.g., a human, e.g., a male human, to determine the subject's risk of developing cardiovascular disease, e.g., coronary artery disease (CAD), ischemic heart disease, atherosclerosis, angina, and myocardial infarction. The method includes determining whether the subject has a polymorphism, e.g., detecting the presence or absence of a polymorphism, e.g., a single nucleotide polymorphism (SNP), in a CD36 gene of the subject. In a preferred embodiment, the method includes determining whether the subject has, in one or both alleles of a CD36 gene of the subject, a polymorphism, e.g., a SNP, in linkage disequilibrium with a nucleotide corresponding to a position listed in FIG. 1. The presence or absence of such a polymorphism is correlated with risk of cardiovascular disease. As used herein, "correlated with" means that that there is a statistically significant association between the polymorphism and risk of cardiovascular disease. The methods can include identifying the polymorphism as a risk or diagnostic factor for cardiovascular disease, e.g., by providing a print material or computer readable medium, e.g., an informational, diagnostic, marketing or instructional print material or computer readable medium, e.g., to the subject or to a health care provider, identifying the polymorphism as a risk or diagnostic factor for cardiovascular disease.

In some embodiments, the presence of a polymorphism in one or both alleles of a CD36 gene of the subject that is in linkage disequilibrium with a nucleotide corresponding to a position listed in FIG. 1 is correlated with an increased risk for cardiovascular disease. In one embodiment, the presence of a polymorphism in linkage disequilibrium with a nucleotide corresponding to position −33137, −31118, 25444, 27645 and/or 30294 listed in FIG. 1 is correlated with an increased risk for cardiovascular disease. Generally, the presence of a polymorphism in linkage disequilibrium with an adenine (A) at the nucleotides corresponding to positions −33137 or −31118 listed in FIG. 1, a guanine (G) at the nucleotide corresponding to position 25444, and/or a cytosine (C) at the nucleotide corresponding to position 30294 listed in FIG. 1, and/or an insertion at the nucleotide corresponding to position 27645 listed in FIG. 1, in one or both alleles of the CD36 gene of the subject, is correlated with an increased risk of developing cardiovascular disease as compared to a reference value, e.g., a value for the comparable risk for a subject not having a polymorphism in linkage disequilibrium with these alleles in one or both chromosomes at the positions −33137, −31118, 25444, 27645 and/or 30294 listed in FIG. 1.

In some embodiments, the methods include determining whether the subject has a polymorphism located within a region of the CD36 gene, e.g., a region defined by the nucleotides corresponding to positions −33137 to 15341 listed in FIG. 1. In another embodiment, the method includes determining whether the subject has a polymorphism located within a region of the CD36 gene defined by the nucleotides corresponding to positions 18672 to 30294 listed in FIG. 1.

In some embodiments, determining whether the subject has a polymorphism can include: (i) providing a probe or primer, e.g., a labeled probe or primer, that includes a region of nucleotide sequence that hybridizes to a sense or antisense sequence from a CD36 gene or naturally occurring mutants thereof, or to the 5' or 3' flanking sequences naturally associated with a CD36 gene; (ii) exposing the probe/primer to nucleic acid of the subject; and (iii) detecting, e.g., by hybridization, e.g., in situ hybridization to the nucleic acid, or by amplification of the nucleic acid, the presence or absence of the polymorphism, e.g., a polymorphism shown in FIG. 1.

In some embodiments, determining includes providing a biological sample of the subject comprising a CD36 gene or fragment thereof, and determining whether the subject has a polymorphism described herein. The detection can be performed by one or more of: chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis, allele specific hybridization, size analysis, nucleotide sequencing, 5' nuclease digestion, primer specific extension, and oligonucleotide ligation assay.

In some embodiments, the methods include diagnosing a subject as being at risk for or having a cardiovascular disease described herein. In some embodiments, the methods include performing a second diagnostic test, e.g., evaluating one or more of: insulin metabolism, plasma glucose levels, plasma lipid levels, urine protein levels, and glomerular filtration rate.

The subject is typically a human, e.g., a human with one or more other risk factors for cardiovascular diseases, e.g., a family history of cardiovascular disease or diabetes. In some embodiments, the subject has a family history of cardiovascular disease, e.g., CAD and/or atherosclerosis, or has an elevated level of a marker of cardiovascular disease, e.g., C reactive protein (CRP). In some embodiments, the subject has diabetes. The biological sample can include a cell sample, tissue sample, or at least partially isolated molecules, e.g., nucleic acids, e.g., genomic DNA, cDNA, mRNA, and/or proteins derived from the subject.

In another aspect, the invention features methods for evaluating a subject, e.g., a human, e.g., a male human, by determining a subject's risk of developing cardiovascular disease. The methods include determining, for one or both alleles of a CD36 gene of the subject, the identity of one or more of the nucleotides corresponding to the positions listed in FIG. 1. In some embodiments, the methods include determining, for one or both alleles of a CD36 gene of the subject, the identity of one of more of the nucleotides corresponding to positions −33137, −31118, 25444, 27645 and/or 30294 listed in FIG. 1. An adenine (A) at the nucleotides corresponding to positions −33137 or −31118 listed in FIG. 1, a guanine (G) at the nucleotide corresponding to position 25444, and/or a cytosine (C) at the nucleotide corresponding to position 30294 listed in FIG. 1, and/or an insertion at the nucleotide corresponding to position 27645 listed in FIG. 1, in one or both alleles of the CD36 gene of the subject, is correlated with an increased risk of developing cardiovascular disease compared to a reference value, e.g., a value for the comparable risk for a subject carrying a different allele in one or both chromosomes at the positions −33137, −31118, 25444, 27645 and/or 30294 listed in FIG. 1.

In some embodiments, determining the identity of a nucleotide can include: (i) providing an oligonucleotide, e.g., a labeled oligonucleotide, that spans a nucleotide corresponding to a position listed in FIG. 1, (ii) exposing the oligonucleotide to nucleic acid of the subject; and/or (iii) detecting, e.g., by hybridization, e.g., in situ hybridization to the nucleic acid, or by amplification of the nucleic acid, the presence or absence of the nucleotide, e.g., a nucleotide corresponding to a position shown in FIG. 1.

In some embodiments, the methods include performing one or more of the following determinations, for one or both chromosomes of the subject:

(a) determining the identity of the nucleotide of the CD36 gene corresponding to position −33137 listed in FIG. 1, e.g., determining if the coding or non coding strand of a CD36 gene of the subject includes an A at the nucleotide corresponding to position −33137 listed in FIG. 1;

(b) determining the identity of the nucleotide of the CD36 gene corresponding to position −31118 listed in FIG. 1, e.g., determining if the coding or non coding strand of a CD36 gene of the subject includes an A at the nucleotide corresponding to position −31118 listed in FIG. 1;

(c) determining the identity of the nucleotide of the CD36 gene corresponding to position 25444 listed in FIG. 1, e.g., determining if the coding or non coding strand of a CD36 gene of the subject includes a G at the nucleotide corresponding to position 25444 listed in FIG. 1;

(d) determining the identity of the nucleotide of the CD36 gene corresponding to position 27645 listed in FIG. 1, e.g., determining if the coding or non coding strand of a CD36 gene of the subject includes an insertion at the nucleotide corresponding to position 27645 listed in FIG. 1; and (e) determining the identity of the nucleotide of the CD36 gene corresponding to position 30294 listed in FIG. 1, e.g., determining if the coding or non coding strand of a CD36 gene of the subject includes a C at the nucleotide corresponding to position 30294 listed in FIG. 1.

In some embodiments, the determining step includes amplifying at least a portion of a CD36 nucleic acid molecule of the subject, e.g., a portion including a nucleotide corresponding to a position listed in FIG. 1.

In some embodiments, the determining step includes sequencing at least a portion of a CD36 nucleic acid molecule of the subject, e.g., a portion including a nucleotide corresponding to a position listed in FIG. 1.

In some embodiments, the determining step includes hybridizing a CD36 nucleic acid molecule of the subject with a probe or primer, e.g., a probe or primer described herein, e.g., a probe or primer including a nucleotide corresponding to a position listed in FIG. 1.

In some embodiments, the method includes generating a dataset of the result of the determination, e.g., generating a print or computer readable material, e.g., an informational, diagnostic, marketing or instructional print material or computer readable medium, e.g., to the subject or to a health care provider, correlating the result of the determination with the subject's risk of developing cardiovascular disease, e.g., CAD.

In another aspect, the invention features kits that include at least one probe or primer described herein, and instructions for using the kit to evaluate risk for cardiovascular disease in a subject. The kit can be used, e.g., by a subject or health care provider.

In another aspect, the invention features computer readable records encoded with at least (a) a subject identifier, e.g., a patient identifier, (b) one or more results from an evaluation of the subject, e.g., a diagnostic evaluation described herein, e.g., the presence or absence of a polymorphism described herein in a CD36 gene of a subject, and optionally (c) a value for or related to a disease state, e.g., a value correlated with disease status or risk with regard to cardiovascular disease. In some embodiments, the invention features a computer medium having a plurality of digitally encoded data records. Each data record includes a value representing the presence or absence of a polymorphism described herein in a biological sample, and/or a descriptor of the sample. The descriptor of the sample can be an identifier of the sample, a subject from which the sample was derived (e.g., a patient), a diagnosis, or a treatment (e.g., a preferred treatment). The data record can be structured as a table, e.g., a table that is part of a database such as a relational database (e.g., a SQL database of the Oracle or Sybase database environments). The invention also includes methods for communicating information about a subject, e.g., by transmitting information, e.g., transmitting a computer readable record described herein, e.g., over a computer network.

As used herein, "hybridization probes" are oligonucleotides of between 5 and 1000 nucleotides that bind in a base-specific manner to a complementary strand of nucleic acid. Such probes include peptide nucleic acids, as described, e.g., in Nielsen et al., Science, 254:1497-1500 (1991). The most appropriate length of the probe may vary depending upon the hybridization method in which it is being used. For example, particular lengths may be more appropriate for use in microfabricated arrays, while other lengths may be more suitable for use in classical hybridization methods. Such optimizations are known to the skilled artisan. For many purposes, suitable probes and primers can range from about 5 to 100, e.g., 5 to 50, or about 5 to about 30 nucleotides in length. For example, probes and primers can be 5, 6, 8, 10, 12, 14, 16, 18, 20, 22, 24, 25, 26, 28 or 30 nucleotides in length. The probe or primer preferably overlaps at least one polymorphism described herein. The nucleotide sequence can correspond to the coding sequence of the allele or to the complement of the coding sequence of the allele.

As used herein, the term "probe" or "primer" refers to a single-stranded oligonucleotide that acts as a point of initiation of template-directed DNA synthesis under appropriate conditions. Such conditions can include, e.g., the presence of four different nucleoside triphosphates and an agent for polymerization, such as DNA or RNA polymerase or reverse transcriptase, an appropriate buffer, and a suitable temperature. The appropriate length of a probe or primer depends on the intended use of the probe or primer, but typically ranges from 10 to 50, e.g., 15 to 30, nucleotides. Short probe or primer molecules generally require cooler temperatures to form sufficiently stable hybrid complexes with the template. A probe or primer need not reflect the exact sequence of the template, but must be sufficiently complementary to hybridize with a template. The terms "probe site" or "primer site" refer to the area of the target DNA to which a probe or primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

As used herein, the term "spanning" means including at least four nucleotides immediately surrounding a reference nucleotide position. The at least four nucleotides can be immediately 5' and/or 3' to the reference nucleotide position.

The term "haplotype" is a set of closely linked alleles (genes or DNA polymorphisms) inherited as a unit. Different combinations of alleles are known as haplotypes. The term "allele" refers to one of the different forms of a gene, DNA sequence, or polymorphism, that can exist at a single locus.

As used herein, the process of "detecting" alleles or polymorphisms is variously described as "genotyping," "determining," or "identifying" an allele or polymorphism, or any similar phrase. The allele actually detected might be a disease-causing mutation, or a mutation that is in linkage disequilibrium with a disease-causing mutation. It will be manifest in the genomic DNA of a patient, but may also be detectable from RNA or protein sequences transcribed or translated from this region.

By "propensity," "predisposition," "susceptibility," or "risk" for disease is meant that certain alleles are statistically associated with a disease, as described herein. They are thus over represented in frequency in individuals with disease as compared to healthy individuals.

As used herein, "linkage disequilibrium" means that genes, alleles, loci and/or genetic markers occur together in the population more frequently than expected on the basis of chance alone. This phenomenon is due to the tendency of genes, alleles, loci and/or genetic markers located on the same chromosome to be inherited together. Linkage disequilibrium can be measured by comparing the population frequency of a combination of genes, alleles, loci and/or genetic markers to the frequency expected on the basis of chance.

The term "polymorphism," as used herein, refers to the occurrence of two or more genetically determined alternative sequences or alleles in a population. The polymorphisms can be those variations (DNA sequence differences) that are generally found between individuals or different ethnic groups and/or geographic locations that, while having a different sequence, produce functionally equivalent gene products. The term can also refer to variants in the sequence that can lead to gene products that are not functionally equivalent. Polymorphisms also encompass variations that can be classified as alleles and/or mutations that can produce gene products that may have an altered function. Polymorphisms also encompass variations that can be classified as alleles and/or mutations that either produce no gene product or an inactive gene product or an active gene product produced at an abnormal rate or in an inappropriate tissue or in response to an inappropriate stimulus.

A "polymorphic marker" or "site" is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic or biallelic polymorphism has two forms. A triallelic polymorphism has three forms.

A "single nucleotide polymorphism" is a polymorphism that occurs at a polymorphic site occupied by a single nucleotide. The site is usually preceded by and/or followed by highly conserved sequences of the allele (e.g., sequences that vary in less than $1/100$ or $1/1000$ members of the populations). A single nucleotide polymorphism usually arises due to substitution of one nucleotide for another at the polymorphic site. A "transition" is the replacement of one purine by another purine or one pyrimidine by another pyrimidine. A "transversion" is the replacement of a purine by a pyrimidine or vice versa. Single nucleotide polymorphisms can also arise from a deletion of a nucleotide or an insertion of a nucleotide relative to a reference allele. Typically the polymorphic site is occupied by a base other than the reference base. For example, where the reference allele contains the base "T" at the polymorphic site, the altered allele can contain a "C," "G," or "A" at the polymorphic site.

The term "isolated" is used herein to indicate that the material in question exists in a physical milieu distinct from that in which it occurs in nature. For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Preferably, an isolated nucleic acid comprises at least about 50, 80 or 90 percent (on a molar basis) of all macromolecular species present.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 1 is a list of characteristics of the SNPs that were investigated at the CD36 locus. Position +1 corresponds to the first nucleotide of the first codon of CD36 coding sequence on the July 2003 Human Genome assembly (hg16), available through UCSC Genome Bioinformatics and the National Center for Biotechnology Information (NCBI, Build 34).

† Relative to the translation start site on the July 2003 Human Genome assembly (hg16).

‡ Frequency of the allele indicated on the right in the 'Variation' column.

¶ The CD36 mRNA has two alternative transcription start sites (exons 1A and 1B) and two alternative 3' UTRs (exons 14 and 15).

§ SNPs representative of the major linkage disequilibrium bins described in the SeattleSNPs Database for the coding region of the CD36 gene.

Figure 2A:
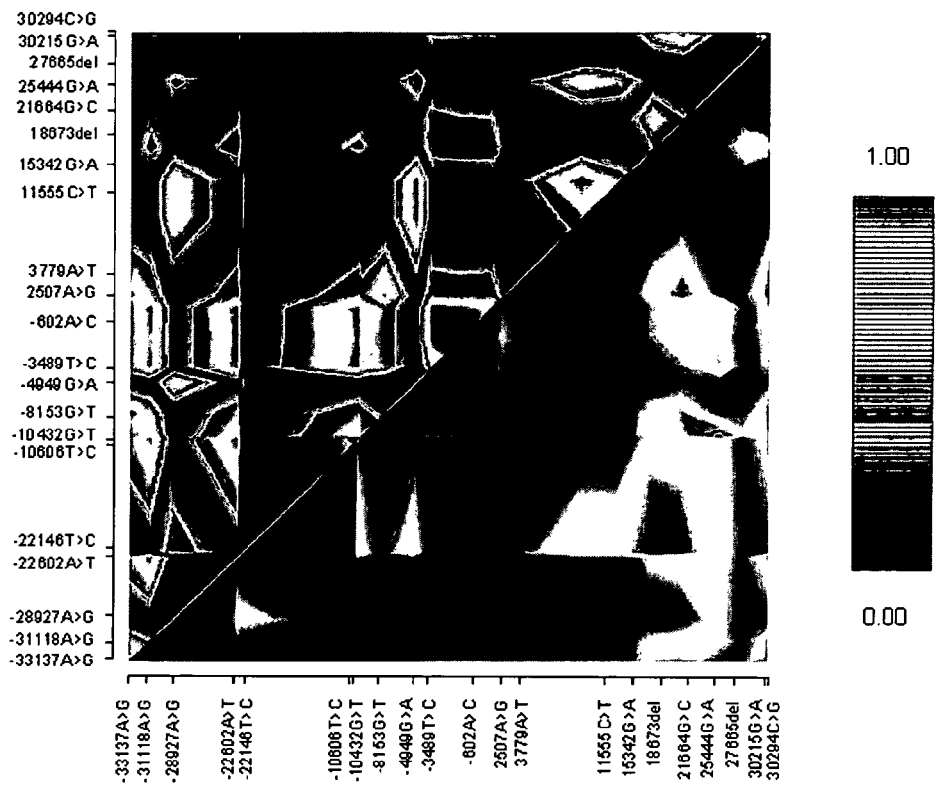
Figure 2B:
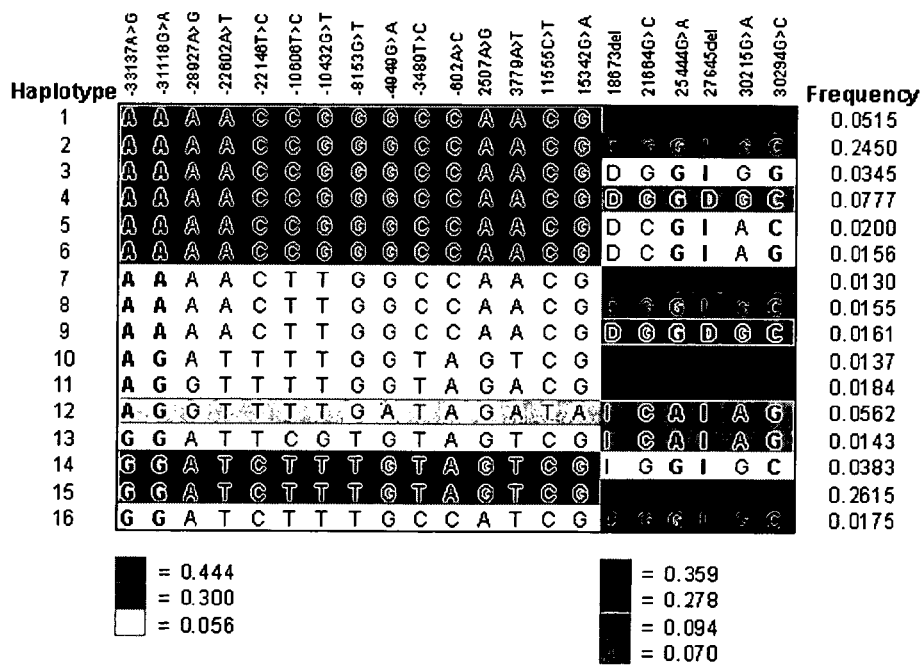

FIGS. 2A and 2B are diagrams of the haplotype blocks at the CD36 locus. (2A) is a diagram of the pairwise linkage disequilibrium (D') between polymorphisms. D' and $r^2$ are reported below and above the diagonal, respectively. Markers are positioned to scale. Two overlapping blocks of preferential LD are visible, one from position 233137 to 15341, the other from position 15341 to 30294. (2B) is a diagram of common haplotypes defined by the polymorphisms. Within each block, common haplotypes are indicated with different shades of gray. Haplotypes that are rare (<0.05) in only one block are indicated in white. Haplotypes that are rare in both blocks are not reported. Haplotype-tagging polymorphisms and the corresponding alleles are indicated in bold.

FIG. 3 is a chart of CD36 haplotypes and free fatty acid (FFA) levels.

FIG. 4A and 4B are graphs of FFA levels (4A) and triglyceride levels (4B) in carriers of different haplotype combinations.

DETAILED DESCRIPTION

The invention is based, at least in part, on the inventors' discovery that certain polymorphisms and/or haplotypes within the CD36 gene correlate with increased risk of cardiovascular disease. The correlation is particularly strong in men and in Type II diabetics.

Atherosclerosis is a frequent and deadly complication of insulin resistance and diabetes (Warram et al., Endocrinol. Metab. Clin. North Am., 26:165-88 (1997)). Vascular dysfunction and atherosclerosis parallel the progression of the disease and may be accelerated by the dyslipidemia as well as the hyperglycemia that are prevalent in poorly controlled diabetes. In the arterial wall, CD36 contributes to the scavenging of oxidized LDL, one of the major triggers of atherosclerotic lesions (Steinberg, J. Biol. Chem., 272:20963-20966 (1997); Endemann et al., J. Biol. Chem., 268:11811-6 (1993)). Thus, genetic variability in the expression or activity of this molecule may have an independent impact on the risk of coronary artery disease, in addition to that due to its effects on free fatty acid (FFA) levels and insulin-sensitivity.

CD36 deficiency, mostly due to a Pro90Ser mutation, has been reported in Japanese and African subjects with a frequency of 2-4% (Kashiwagi et al., J. Clin. Invest. 95:1040-6 (1995); Hirano et al., Med. 13:136-41 (2003)). In Japanese, CD36 deficiency has been associated with impaired glucose disposal in response to insulin and increased levels of FFA, triglycerides, fasting blood glucose, and blood pressure (Miyaoka et al., Lancet, 357:686-7 (2001)). Other studies have confirmed the association with higher plasma FFA, but not with other insulin-resistance traits (Furuhashi et al., Diabetes Care, 26:471-4 (2003); Kajihara et al., Clin. Chim. Acta., 314:125-30 (2001)). No data are available for Caucasians, owing to the rarity of the Pro90Ser mutation in this racial group (<0.3%).

In a population of non-diabetic individuals of Caucasian ancestry, the present inventors found that one of the few common haplotypes occurring at this locus (AAGIC) is associated with increased fasting levels of FFA and triglycerides. These findings are unlikely to be due to chance. First, the P-value for the association with FFA is highly significant. Second, the same haplotype associated with FFA was significantly associated with a related phenotype (CAD) in an independent study, and a similar tendency was observed in yet another population. Nonetheless, the results of association studies must always be interpreted with caution (Ioannidis et al., Nat. Genet., 29:306-309 (2001), Lohmueller et al., Nat. Genet., 33, 177-182 (2003)), especially when multiple comparisons are performed, and replication in other settings is needed before a link between CD36 variability, FFA metabolism and cardiovascular disease is firmly established.

Methods of Detecting CD36 Polymorphisms

The methods described herein, e.g., diagnostic and prognostic methods described herein, can include evaluating one or more CD36 polymorphisms. Methods described herein provide for determining whether a subject carries a polymorphism of the CD36 gene. For example, methods are provided for determining which allele or alleles of the human CD36 gene a subject carries.

Biological Samples

Polymorphisms can be detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed.

Amplification of DNA from target samples can be accomplished by methods known to those of skill in the art, e.g., polymerase chain reaction (PCR). See, e.g., U.S. Pat. No.

4,683,202 (which is incorporated herein by reference in its entirety), ligase chain reaction (LCR) (see Wu and Wallace, Genomics, 4:560 (1989); Landegren et al., Science, 241:1077 (1988)), transcription amplification (Kwoh et al., Proc. Natl. Acad. Sci. USA, 86:1173 (1989)), self-sustained sequence replication (Guatelli et al., Proc. Natl. Acad. Sci. USA, 87:1874 (1990)), and nucleic acid based sequence amplification (NASBA). A variety of suitable procedures that can be employed to detect polymorphisms are described in further detail below.

Allele-Specific Probes

The design and use of allele-specific probes for analyzing polymorphisms is known in the art (see, e.g., Dattagupta, EP 235,726; Saiki, WO 89/11548). Allele-specific probes can be designed to hybridize differentially, e.g., to hybridize to a segment of DNA from one individual but not to a corresponding segment from another individual, based on the presence of polymorphic forms of the segment. Relatively stringent hybridization conditions can be utilized to cause a significant difference in hybridization intensity between alleles, and possibly to obtain a condition wherein a probe hybridizes to only one of the alleles. High stringency conditions include TMAC (tetramethylammonium chloride), SDS, EDTA, Denhart's Solution, and yeast tRNA at 52° C. Probes can be designed to hybridize to a segment of DNA such that the polymorphic site aligns with a central position of the probe.

Allele-specific probes can be used in pairs, wherein one member of the pair matches perfectly to a reference form of a target sequence, and the other member of the pair matches perfectly to a variant of the target sequence. The use of several pairs of probes immobilized on the same support may allow simultaneous analysis of multiple polymorphisms within the same target sequence.

Tiling Arrays

Polymorphisms can also be identified by hybridization to nucleic acid arrays (see, e.g., WO 95/11995). WO 95/11995 also describes subarrays that are optimized for the detection of variant forms of a precharacterized polymorphism. Such a subarray contains probes designed to be complementary to a second reference sequence, which is an allelic variant of the first reference sequence. The second group of probes is designed to exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

Allele-Specific Primers

An allele-specific primer hybridizes to a site on target DNA overlapping a polymorphism and only primes amplification of an allelic form to which the primer exhibits perfect complementarily. See, e.g., Gibbs, Nucleic Acid Res., 17:2427-2448 (1989). Such a primer can be used in conjunction with a second primer that hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method can be optimized by including the mismatch in the 3'-most position of the oligonucleotide aligned with the polymorphism because this position is most destabilizing to elongation from the primer. See, e.g., WO 93/22456.

Direct-Sequencing

The direct analysis of the sequence of polymorphisms of the present invention can be accomplished using, e.g., the dideoxy chain termination method or the Maxam Gilbert method (see, e.g., Sambrook et al., *Molecular Cloning: A Laboratory Manual,* 3d ed., 2001, Cold Spring Harbor, which is hereby incorporated in its entirety; Zyskind et al., *Recombinant DNA Laboratory Manual,* Acad. Press, 1988).

Single Base Extension

Polymorphisms described herein can be sequenced using single base extension (SBE), a dideoxy chain termination sequencing procedure in which only the polymorphic site is sequenced, followed by fluorescence polarization (FP) analysis (e.g., using the AcycloPrime™-FP SNP Detection System, Perkin-Elmer). This assay is based on the principle that incorporation of a fluorescent terminator into a primer oligonucleotide increases its polarization (see, e.g., Hsu et al., Biotechniques, 31:560-570 (2001)). A nucleotide at a polymorphic site can be determined by using different fluorescent terminators in the SBE reactions. For example, SNP-containing PCR products can be amplified from study subjects in 96-well plates using primers described herein. After shrimp alkaline phosphatase treatment to inactivate unincorporated dNTPs and primers, PCR products can undergo SBE using a primer described herein and fluorescent terminators. Fluorescence polarization can be determined using, e.g., a Wallac VICTOR$^2$™ Multilabel Plate Reader (Perkin-Elmer).

Denaturing Gradient Gel Electrophoresis

Amplification products generated using the polymerase chain reaction can be analyzed, e.g., by the use of denaturing gradient gel electrophoresis. Different alleles can be identified based on the different sequence-dependent melting properties and electrophoretic migration of DNA in solution. See, e.g., Erlich, ed., *PCR Technology, Principles and Applications for DNA Amplification,* W.H. Freeman and Co, New York, 1992, Chapter 7.

Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., Proc. Natl. Acad. Sci. USA, 86:2766-2770 (1989). Amplified PCR products can be generated as described above, and heated or otherwise denatured, to form single stranded amplification products. Single-stranded nucleic acids may refold or form secondary structures that are partially dependent on the base sequence. The different electrophoretic mobilities of single-stranded amplification products can be related to base-sequence difference between alleles of target sequences.

Other methods of detecting polymorphisms, e.g., SNPs, are known, e.g., as described in U.S. Pat. No. 6,410,231; U.S. Pat. No. 6,361,947; U.S. Pat. No. 6,322,980; U.S. Pat. No. 6,316,196; and U.S. Pat. No. 6,258,539.

Detection Of Variations Or Mutations

Alterations or mutations in a CD36 gene can be identified by a number of methods known in the art, to thereby identify other polymorphisms that may be associated with susceptibility for CAD. In preferred embodiments, the methods include detecting, in a sample from the subject, the presence or absence of a genetic alteration characterized by an alteration affecting the integrity of a gene encoding a CD36 protein, or the mis-expression of the CD36 gene. For example, such genetic alterations can be detected by ascertaining the existence of at least one of 1) a deletion of one or more nucleotides from a CD36 gene; 2) an addition of one or more nucleotides to a CD36 gene; 3) a substitution of one or more nucleotides of a CD36 gene, 4) a chromosomal rearrangement of a CD36 gene; 5) an alteration in the level of a messenger RNA transcript of a CD36 gene; 6) aberrant modification of a CD36 gene, such as of the methylation pattern of the genomic DNA; 7) the presence of a non-wild type splicing pattern of a messenger RNA transcript of a CD36 gene; 8) a non-wild type level of a CD36 protein; 9) allelic loss of a CD36 gene; and 10) inappropriate post-translational modification of a CD36 protein.

An alteration can be detected with or without a probe/primer in a polymerase chain reaction, e.g., by anchor PCR or RACE PCR, or, alternatively, in a ligation chain reaction (LCR), the latter of which can be particularly useful for detecting point mutations in the CD36 gene. This method can include the steps of collecting a sample of cells from a subject, isolating nucleic acid (e.g., genomic, mRNA or both) from the sample, contacting the nucleic acid sample with one or more primers which specifically hybridize to a CD36 gene under conditions such that hybridization and amplification of the CD36 gene (if present) occurs, and detecting the presence or absence of an amplification product, or detecting the size of the amplification product and comparing the length to a control sample. PCR and/or LCR can be used as a preliminary amplification step in conjunction with any of the techniques used for detecting mutations described herein. Alternatively, other amplification methods described herein or known in the art can be used.

In another embodiment, mutations in a CD36 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in CD36 can be identified by hybridizing a sample and control nucleic acids, e.g., DNA or RNA, to two-dimensional arrays, e.g., chip based arrays. Such arrays include a plurality of addresses, each of which is positionally distinguishable from the other. A different probe is located at each address of the plurality. A probe can be complementary to a region of a CD36 nucleic acid or a putative variant (e.g., allelic variant) thereof. A probe can have one or more mismatches to a region of a CD36 nucleic acid (e.g., a destabilizing mismatch). The arrays can have a high density of addresses, e.g., can contain hundreds or thousands of oligonucleotides probes (Cronin et al., Human Mutation, 7:244-255 (1996); Kozal et al., Nature Medicine, 2:753-759 (1996)). For example, genetic mutations in CD36 can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CD36 gene and to detect mutations by comparing the sequence of the sample CD36 with the corresponding wild-type (control) sequence. Automated sequencing procedures can be utilized when performing the diagnostic assays (Naeve et al., Biotechniques, 19:448-453 (1995)), including sequencing by mass spectrometry.

Other methods for detecting mutations in the CD36 gene include methods in which protection from cleavage agents is used to detect mismatched bases in RNA/RNA or RNA/DNA heteroduplexes (Myers et al., Science, 230:1242-1246 (1985); Cotton et al., Proc. Natl. Acad. Sci. USA, 85:4397-4401 (1988); Saleeba et al., Methods Enzymol., 217:286-295 (1992)).

In still another embodiment, the mismatch cleavage reaction employs one or more proteins that recognize mismatched base pairs in double-stranded DNA (so called "DNA mismatch repair" enzymes) in defined systems for detecting and mapping point mutations in CD36 cDNAs obtained from samples of cells. For example, the mutY enzyme of E. coli cleaves A at G/A mismatches and the thymidine DNA glycosylase from HeLa cells cleaves T at G/T mismatches (Hsu et al., Carcinogenesis, 15:1657-1662 (1994); U.S. Pat. No. 5,459,039).

In other embodiments, alterations in electrophoretic mobility will be used to identify mutations in CD36 genes. For example, single strand conformation polymorphism (SSCP) may be used to detect differences in electrophoretic mobility between mutant and wild type nucleic acids (Orita et al., Proc. Natl. Acad. Sci. USA, 86:2766 (1989); see also Cotton, Mutat. Res., 285:125-144 (1993); and Hayashi, Genet. Anal. Tech. Appl., 9:73-79 (1992)). Single-stranded DNA fragments of sample and control CD36 nucleic acids will be denatured and allowed to renature. The secondary structure of single-stranded nucleic acids varies according to sequence; the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., Trends Genet., 7:5 (1991)).

In yet another embodiment, the movement of mutant or wild-type fragments in polyacrylamide gels containing a gradient of denaturant is assayed using denaturing gradient gel electrophoresis (DGGE) (Myers et al., Nature, 313:495-498 (1985)). When DGGE is used as the method of analysis, DNA will be modified to ensure that it does not completely denature, for example, by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum et al., Biophys. Chem., 26:235-246 (1987)).

Examples of other techniques for detecting point mutations include, but are not limited to, selective oligonucleotide hybridization, selective amplification, or selective primer extension (Saiki et al., Nature, 324:163-166 (1986); Saiki et al., Proc. Natl. Acad. Sci. USA, 86:6230-6234 (1989)). A further method of detecting point mutations is the chemical ligation of oligonucleotides as described in Xu et al., Nature Biotechnol., 19:148-152 (2001). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al., Nucleic Acids Res., 17:2437-2448 (1989)), or at the extreme 3' end of one primer where, under appropriate conditions, mismatch can prevent, or reduce polymerase extension (Prosser, Trends Biotechnol., 11(6):238-246 (1993)). In addition, it may be desirable to introduce a novel restriction site in the region of the mutation to create cleavage-based detection (Gasparini et al., Mol. Cell Probes, 6:1-7 (1992)). It is anticipated that in certain embodiments amplification may also be performed using Taq ligase for amplification (Barany, Proc. Natl. Acad. Sci. USA, 88:189-193 (1991)). In such cases, ligation will occur only if there is a perfect match at the 3' end of the 5' sequence, making it possible to detect the presence of a known mutation at a specific site by looking for the presence or absence of amplification.

Diagnostic Assays

The diagnostic assays described herein involve evaluating genetic variability, e.g., the presence or absence of polymorphisms, within one or both alleles of a CD36 gene in a subject.

Genotype Screening

Genetic screening (also called genotyping or molecular screening), can be broadly defined as testing to determine if a patient has mutations, e.g., polymorphisms, that either cause a disease state or are "linked" to the mutation causing a disease state. Linkage refers to the phenomenon that DNA sequences that are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given human population, they tend to either both occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

While the frequency of meiotic recombination between two markers is generally proportional to the physical distance between them on the chromosome, the occurrence of "hot spots" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage with this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore, identification of a human haplotype that spans or is linked to a disease-causing mutational change serves as a predictive measure of an individual's likelihood of having inherited that disease causing, e.g., cardiovascular disease-causing, mutation. Importantly, such prognostic or diagnostic procedures can be utilized without necessitating the identification and isolation of the actual disease-causing lesion. This is significant because the precise determination of the molecular defect involved in a disease process can be difficult and laborious, especially in the case of multifactorial diseases such as inflammatory disorders.

Indeed, the statistical correlation between a disorder and polymorphism does not necessarily indicate that the polymorphism directly causes the disorder. Rather the correlated polymorphism may be a benign allelic variant that is linked to (i.e. in linkage disequilibrium with) a disorder-causing mutation that has occurred in the recent human evolutionary past, so that sufficient time has not elapsed for equilibrium to be achieved through recombination events in the intervening chromosomal segment. Thus, for the purposes of diagnostic and prognostic assays for a particular disease, detection of a polymorphic allele associated with that disease can be utilized without consideration of whether the polymorphism is directly involved in the etiology of the disease. Furthermore, where a given benign polymorphic locus is in linkage disequilibrium with an apparent disease-causing polymorphic locus, still other polymorphic loci that are in linkage disequilibrium with the benign polymorphic locus are also likely to be in linkage disequilibrium with the disease-causing polymorphic locus. Thus these other polymorphic loci will also be prognostic or diagnostic of the likelihood of having inherited the disease-causing polymorphic locus. Indeed, a broad-spanning human haplotype (describing the typical pattern of co-inheritance of alleles of a set of linked polymorphic markers) can be targeted for diagnostic purposes once an association has been drawn between a particular disease or condition and a corresponding human haplotype. Thus, the determination of an individual's likelihood for developing a particular disease of condition can be made by characterizing one or more disease-associated polymorphic alleles (or even one or more disease-associated haplotypes) without necessarily determining or characterizing the causative genetic variation.

Linkage disequilibrium can be determined using routine methods, e.g., using the GOLD software package (Schaid et al., Am. J. Hum. Genet., 70:425-34 (2002)) and the Haplo Stats suite (Zhang et al., Proc. Natl. Acad. Sci. USA, 99:7335-9 (2002)).

Expression Monitoring and Profiling

The presence, level, or absence of CD36 (protein or nucleic acid) in a biological sample can be evaluated by obtaining a biological sample from a test subject and contacting the biological sample with a compound or an agent capable of detecting the protein or nucleic acid (e.g., mRNA, genomic DNA) that encodes CD36 such that the presence of the protein or nucleic acid is detected in the biological sample. The term "biological sample" includes tissues, cells and biological fluids isolated from a subject, as well as tissues, cells and fluids present within a subject, e.g., urine. Preferred biological samples are serum or urine. The level of expression of CD36 can be measured in a number of ways, including, but not limited to: measuring the mRNA encoded by the CD36 gene; measuring the amount of protein encoded by CD36; or measuring the activity of the protein encoded by the gene.

The level of mRNA corresponding to CD36 in a cell can be determined both by in situ and by in vitro methods.

Isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length nucleic acid, or a portion thereof, such as an oligonucleotide of at least 7, 15, 30, 50, 100, 250 or 500 nucleotides in length and sufficient to specifically hybridize under stringent conditions to mRNA or genomic DNA of CD36. The probe can be disposed on an address of an array, e.g., an array described herein. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described herein. A skilled artisan can adapt known mRNA detection methods for use in detecting the level of mRNA encoded by the gene.

The level of mRNA in a sample that is encoded by a gene can be evaluated with nucleic acid amplification, e.g., by rtPCR (Mullis, U.S. Pat. No. 4,683,202), ligase chain reaction (Barany, supra), self sustained sequence replication (Guatelli et al., Proc. Natl. Acad. Sci. USA, 87:1874-1878 (1990)), transcriptional amplification system (Kwoh et al., Proc. Natl. Acad. Sci. USA, 86:1173-1177 (1989)), Q-Beta Replicase (Lizardi et al., Bio/Technology, 6:1197 (1988)), rolling circle replication (Lizardi et al., U.S. Pat. No. 5,854,033), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the gene being analyzed.

In another embodiment, the methods further include contacting a control sample with a compound or agent capable of detecting mRNA, or genomic DNA, and comparing the presence of the mRNA or genomic DNA in the control sample with the presence of CD36 mRNA or genomic DNA in the test sample. In still another embodiment, serial analysis of gene expression (as described in, e.g., U.S. Pat. No. 5,695,937) is used to detect transcript levels of CD36.

A variety of methods can be used to determine the level of CD36 protein. In general, these methods include contacting an agent that selectively binds to the protein, such as an antibody, with a sample to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect CD36 in a biological sample in vitro as well as in vivo. In vitro techniques for detection include enzyme linked immunosorbent assays (ELISAs), immunoprecipitations, immunofluorescence, enzyme immunoassay (EIA), radioimmunoassay (RIA), and Western blot analysis. In vivo techniques for detection of CD36 include introducing into a subject a labeled antibody. For example, the antibody can be labeled with a radioactive marker whose presence and location in a subject can be detected by standard imaging techniques. In another embodiment, the sample is labeled, e.g., biotinylated, and then contacted to the antibody, e.g., an antibody positioned on an antibody array. The sample can be detected, e.g., with avidin coupled to a fluorescent label.

In another embodiment, the methods further include contacting the control sample with a compound or agent capable of detecting CD36, and comparing the presence of CD36 protein in the control sample with the presence of the protein in the test sample.

The invention also includes kits for detecting the presence of CD36 in a biological sample. For example, the kit can include a compound or agent capable of detecting CD36 protein (e.g., an antibody) or mRNA (e.g., a nucleic acid probe); and a standard. The compound or agent can be packaged in a suitable container. The kit can further include instructions for using the kit to evaluate a subject, e.g., for risk of cardiovascular disease, e.g., CAD.

The diagnostic methods described herein can identify subjects having, or at risk of developing, cardiovascular disease, e.g., CAD. The prognostic assays described herein can be used to determine whether a subject can be administered an agent to treat cardiovascular disease, e.g., CAD.

Kits

An agent useful to evaluate a CD36 polymorphism, e.g., a probe or primer described herein, can be provided in a kit. The kit includes (a) the agent, e.g., a CD36 primer or probe, and (b) informational material. The informational material can be descriptive, instructional, marketing or other material that relates to the methods described herein and/or the use of the agent, e.g., a CD36 primer or probe, for the methods described herein. For example, the informational material relates to cardiovascular disease, e.g., to evaluation of risk for cardiovascular disease.

In one embodiment, the informational material can include instructions to use the agent in a suitable manner to perform the methods described herein, e.g., instructions to use the agent in polymerase chain reaction (PCR).

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about the agent and/or its use in the methods described herein. Of course, the informational material can also be provided in any combination of formats.

In addition to an agent used to evaluate a CD36 polymorphism, the composition of the kit can include other ingredients, such as a solvent or buffer, a stabilizer, or a preservative. Alternatively, the other ingredients can be included in the kit, but in different compositions or containers than the agent. In such embodiments, the kit can include instructions for admixing the agent and the other ingredients, or for using the agent together with the other ingredients.

The agent can be provided in any form, e.g., liquid, dried or lyophilized form. It is preferred that the agent be substantially pure and/or sterile. When the agent is provided in a liquid solution, the liquid solution preferably is an aqueous solution, with a sterile aqueous solution being preferred. When the agent is provided as a dried form, reconstitution generally is by the addition of a suitable solvent. The solvent, e.g., sterile water or buffer, can optionally be provided in the kit.

The kit can include one or more containers for the composition containing the agent. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit forms of the agent. For example, the kit includes a plurality of syringes, ampoules, foil packets, or blister packs, each containing a single unit form of the agent. The containers of the kits can be air tight and/or waterproof.

The invention is further described in the following examples, which do not limit the scope of the invention described in the claims.

EXAMPLES

Example 1

Determination of the Haplotype Structure of the CD36 Locus

To determine the haplotype structure of the CD36 locus in Caucasians, 21 common SNPs (frequency≧0.05) were typed in 72 unrelated individuals from the general population. Study subjects were genotyped at polymorphic loci by means of PCR followed by dot blotting and allelic specific hybridization or single base extension/fluorescence polarization (AcycloPrime™-FP SNP Detection System) using a Wallac VICTOR²™ Multilabel Plate Reader (Perkin-Elmer).

Eight of the 21 SNPs were representative of the major linkage disequilibrium bins identified in the region between intron 3 and exon 14 by a resequencing project (available at pga.gs.washington.edu/data/cd36/). The other eleven were selected from the dbSNP database to cover the two alternative promoters (Sato et al., J. Biol. Chem., 277:15703-11 (2002)), the 5' non-coding exons, and the 3' UTR in exon 15. The 21 SNPs spanned a total of 63 Kb, resulting in a 3.0 Kb average spacing (FIG. 1).

Genotype distributions were tested at each polymorphic locus for departure from Hardy-Weinberg equilibrium. Pairwise linkage disequilibrium coefficients (D') were estimated using the GOLD software package (Schaid et al., Am. J. Hum. Genet., 70:425-34 (2002)). Maximum likelihood estimates of haplotype frequencies were derived using the EM algorithm as implemented in the function haplo.em of the Haplo Stats suite (Zhang et al., Proc. Natl. Acad. Sci. USA, 99:7335-9 (2002)). Haplotype block partitioning and the htSNP selection were conducted by means of the dynamic programming algorithms implemented in the HapBlock software (Laws et al., Arterioscler. Thromb. Vasc. Biol., 17:64-71 (1997)), with α (minimal proportion of chromosomes accounted by common [≧0.05]haplotypes)=80%.

Significant linkage disequilibrium (LD) was observed across the entire locus (FIG. 2A). However, two blocks of preferential LD appeared to be present, one extending from position −33137 to 15554, the other covering the remaining 15 kb (FIG. 2A). This pattern was confirmed by haplotype analysis and the block-partitioning algorithm implemented in the HapBlock software (Laws et al., Arterioscler. Thromb. Vasc. Biol., 17:64-71 (1997)). If the two blocks were considered separately, common (≧5%) haplotypes accounted for 80% of the haplotypes in the first block and 80% of those in the second block (FIG. 2B; within each block, common haplotypes are indicated with different shades of grey; haplotypes that are rare (<0.05) in only one block are indicated in white, and haplotypes that are rare in both blocks are not reported). By contrast, if the entire locus was considered as a single block, common haplotypes accounted for only 69% of the chromosomes. Based on these findings, five haplotype tagging SNPs (htSNPs) were selected, two from the first block (−33137A>G and −31118A>G), and three from the second block (25444G>A, 27645del, and 30294C>G) (FIG. 2B).

Example 2

Demonstration of an Association Between FFA Levels and CD36 SNPs

The association between CD36 variants and metabolic traits was evaluated in 585 Caucasian residents of the Gargano area (East Coast of Italy). Their clinical characteristics are reported in Table 1. Subjects were recruited among the employees of the hospital 'Casa Sollievo della Sofferenza' (San Giovanni Rotondo, Italy), who had fasting plasma glucose <7 mmol/l at screening and were not taking any medications. The study protocol and informed consent procedures were approved by the local research ethic committee. All study subjects were examined between 8:00 and 9:00 AM after an overnight fast. Height and weight were used to calculate body mass index (BMI) and percent ideal body weight (% IBW, calculated by multiplying BMI by 4.39 for males and 4.76 for females). Waist circumference (the widest value between the lower rib margin and the iliac crest) was measured with a plastic measuring tape by the same investigator in all subjects while standing. Systolic and diastolic (disappearance of Korotkoff sound, phase V) blood pressures were measured in the sitting position with an appropriately sized cuff after a 5-minute rest. Plasma glucose (mmol/l), serum insulin (pmol/l) and lipid profile (total serum cholesterol, HDL cholesterol, serum triglycerides) were measured using commercially available enzymatic kits as previously described (Shimuzu et al., Anal. Biochem., 98:341-345 (1978)). Plasma free fatty acids were determined using a microenzymatic assay as described by Shimuzu et al. (Ellestad, *Stress testing. Principles and Practice*, F A Davis, Philadelphia. (1986)). The inter-and intra-assay coefficients of variation were 2.2% and 2.8%, respectively.

Continuous variables were compared among genotype groups by ANOVA using the PROC GLM procedure of the SAS software package (SAS Institute, Cary, N.C.). All analyses included gender and age as covariates. Fasting insulin, triglycerides, and FFA were analyzed after logarithmic transformation. The association between FFA levels and common ($\geqq 0.05$) CD36 haplotypes was analyzed using the score statistics proposed by Schaid et al. and implemented in the function HAPLO.SCORE of the Haplo Stats software (Schaid et al., Am. J. Hum. Genet., 70:425-34 (2002)). This method allows adjustment for non-genetic covariates (age, gender) and provides a global test of association as well as haplotype-specific tests. After testing for association with haplotypes, diplotypes were assigned to each individual on the basis of the posterior probabilities of the different phases.

Salient clinical characteristics of study subjects according to gender are reported in Table 1. In addition to the expected anthropometric and metabolic differences between genders, men had significantly lower FFA levels than women (p=0.029). FFA levels were correlated in men with % IBW (r=0.28, p<0.0001), waist circumference (r=0.23, p=0.0008), HOMAIR (r=0.20, p=0.004), and triglycerides (r=0.30, p<0.0001). Such correlations were much weaker or absent in women despite a similar range of FFA variation and a larger sample size (r=0.14 for % IBW, r=0.12 for waist, r=0.02 for HOMAIR, r=0.12 for triglycerides). Thus, FFA metabolism appeared to be under different control in the two genders, consistent with previous reports in the literature (Perseghin et al., J. Clin. Endocrinol. Metab., 86:3188-96 (2001); Omi et al., Am. J. Hum. Genet., 72:364-74 (2003)).

TABLE 1

Clinical characteristic of study subjects according to gender.

|  | Men | Women | p |
|---|---|---|---|
| n | 231 | 354 |  |
| Age (years) | 36 ± 12 | 36 ± 12 | 0.82 |
| % IBW | 115 ± 17 | 118 ± 23 | 0.066 |
| Waist (cm) | 90.4 ± 11 | 77.8 ± 11 | <0.0001 |
| Systolic blood pressure (mmHg) | 118 ± 12 | 112 ± 12 | <0.0001 |
| Diastolic blood pressure (mmHg) | 80 ± 9 | 74 ± 9 | <0.0001 |
| Fasting blood glucose (mg/dl) | 92 ± 9 | 88 ± 9 | 0.0001 |
| Serum insulin (µU/ml) | 7.99 ± 4.8 | 7.51 ± 4.2 | 0.45 |
| HOMA$_{IR}$ | 1.82 ± 1.2 | 1.64 ± 1.0 | 0.086 |
| Cholesterol (mg/dl) | 196 ± 42 | 191 ± 38 | 0.15 |
| HDL cholesterol (mg/dl) | 46 ± 12 | 57 ± 12 | <0.0001 |
| Total/HDL cholesterol ratio | 4.5 ± 1.5 | 3.4 ± 0.9 | <0.0001 |
| Triglycerides (mg/dl) | 115 ± 72 | 76 ± 39 | <0.0001 |
| FFA (mmol/l) | 0.543 ± 0.238 | 0.576 ± 0.226 | 0.029† |

Data are mean ± SD.
†p = 0.0001 when adjusted for waist circumference.

Genotype distributions were in Hardy-Weinberg equilibrium at all five loci. Three of the five htSNPs (−33137, −31118, and 30294) showed a significant dose-response effect between the major allele and FFA levels (p=0.021, 0.05, and 0.048, respectively). A significant interaction between this effect and gender was observed at positions −33137 and −31118 (p=0.02 and 0.016, respectively), and a similar tendency was observed for SNP 30294 (p=0.069). Indeed, when data were stratified by gender, the association between the three SNPs and FFA levels concerned only men (Table 2). At each of the three loci, men homozygous for one allele had 30% higher FFA levels than men homozygous for the other allele, with heterozygotes having intermediate values (p=0.002, p=0.006, and p=0.009 for −33137, −31118, and 30294, respectively) (Table 2). A similar pattern of association was observed for serum triglycerides at position −33137 (122±69 mg/dl in A/A; 111±62 mg/dl in A/G; and 101±74 mg/dl in G/G; p=0.027). No other metabolic traits or anthropometric measures were associated with the five htSNPs in either men or women.

TABLE 2

FFA levels according to gender and CD36 SNP genotypes.

|  | Men | | | Women | | |
|---|---|---|---|---|---|---|
| SNP | n | FFA (mmol/l) | p | n | FFA (mmol/l) | p |
| −33137 |  |  |  |  |  |  |
| A/A | 65 | 0.621 ± 0.247 |  | 88 | 0.572 ± 0.233 |  |
| A/G | 105 | 0.543 ± 0.252 |  | 181 | 0.582 ± 0.240 |  |
| G/G | 47 | 0.472 ± 0.172 | 0.002 | 61 | 0.556 ± 0.209 | 0.78 |
| −31118 |  |  |  |  |  |  |
| A/A | 45 | 0.613 ± 0.281 |  | 70 | 0.553 ± 0.204 |  |
| A/G | 105 | 0.557 ± 0.246 |  | 168 | 0.587 ± 0.251 |  |
| G/G | 64 | 0.471 ± 0.187 | 0.006 | 90 | 0.560 ± 0.197 | 0.82 |
| 25444 |  |  |  |  |  |  |
| G/G | 166 | 0.545 ± 0.256 |  | 234 | 0.558 ± 0.209 |  |
| G/A + A/A | 18 | 0.583 ± 0.207 | 0.36 | 34 | 0.586 ± 0.209 | 0.35 |
| 27645 |  |  |  |  |  |  |
| I/I | 189 | 0.540 ± 0.237 |  | 294 | 0.569 ± 0.219 |  |
| I/D + D/D | 34 | 0.577 ± 0.243 | 0.38 | 45 | 0.619 ± 0.257 | 0.24 |
| 30294 |  |  |  |  |  |  |
| C/C | 57 | 0.586 ± 0.273 |  | 97 | 0.569 ± 0.210 |  |
| C/G | 111 | 0.561 ± 0.236 |  | 149 | 0.596 ± 0.242 |  |
| G/G | 37 | 0.448 ± 0.179 | 0.009 | 67 | 0.555 ± 0.229 | 0.59 |

When the htSNPs were considered together, a significant association between CD36 haplotypes and FFA was detected in both blocks among men (global p=0.03 and 0.02 for the first and second block, respectively). In the first block, the AA haplotype was associated with high FFA levels, and the GG haplotype with low levels (haplotype-specific p=0.005 and 0.007, respectively) (FIG. 3; positive and negative scores denote an association with high and low FFA levels, respectively. Haplotype specific p-values are reported along with global p-values for the two blocks considered separately and together.). In the second block, the GIC haplotype was associated with high FFA levels, and the GIG haplotype with low levels (p=0.044 and p=0.002, respectively) (FIG. 3). When the two blocks were considered together, the AA haplotype of the first block was significantly associated with high FFA levels only in association with the GIC haplotype of the second block (haplotype AAGIC, p=0.001). Conversely, the GG haplotype was significantly associated with low FFA levels only in combination with the GIG haplotype (haplotype GGGIG, p=0.02). Once diplotypes were assigned to individuals, FFA levels were similarly high in carriers of one or two copies of the AAGIC haplotype (p=0.45). These subjects (including AAGIC/GGGIG subjects) had 31% higher FFA levels than individuals not carrying the AAGIC haplotype (p=0.0002) (FIG. 4; data are mean±SE and 'X' denotes any haplotype other than AAGIC and GGGIG). A similar pattern was observed for triglycerides (20% increase in AAGIC carriers, p=0.025), but not for fasting insulin or other metabolic traits. No association between CD36 haplotypes and FFA or triglycerides levels was observed in women.

Example 3

Demonstration of an Association Between CAD and CD36 SNPs

To determine whether the CD36 AAGIC haplotype was also associated with coronary artery disease (CAD), two populations of individuals with type 2 diabetes (defined according to the WHO criteria) were studied, one from Boston (n=197), the other from San Giovanni Rotondo, Italy (n=321). The study protocol and informed consent procedures were approved by the local research ethic committees. Each population included a group of CAD-positive cases and a group of CAD-negative controls. In the Boston study, the CAD-positive cases, defined as subjects who had a stenosis greater than 50% in at least one major coronary artery or their main branches, were recruited among type 2 diabetic patients who underwent cardiac catheterization at the Beth Israel Deaconess Medical Center (BIDMC) between Feb. 1, 2000, and Jan. 31, 2002. CAD-negative controls were Joslin patients (the Joslin Clinic serves as the BIDMC Diabetes Clinic) who were age 55 or older, had had diabetes for five years or more, and had a negative cardiovascular history and a normal exercise treadmill test (ETT) according to a standard Bruce protocol (Abecasis and Cookson, Bioinformatics, 16:182-3 (2000)). The San Giovanni Rotondo sample consisted of type 2 diabetic patients who attended the local institution from January 2002 to July 2003. Cases were patients who had angiographic evidence of stenosis greater than 50% in at least one major coronary artery or their main branches, or who had acute myocardial infarction. Controls included diabetic patients without symptoms and with normal resting ECG and ETT or with coronary stenosis (at angiography)≦50%. Clinical features of cases and controls from the two studies are shown in Table 3.

TABLE 3

Clinical characteristics of CAD-positive cases and CAD-negative controls with type 2 diabetes from Boston and from Italy.

|  | Boston | | | Italy | | |
| --- | --- | --- | --- | --- | --- | --- |
|  | CAD− | CAD+ | p | CAD− | CAD+ | p |
| N | 79 | 118 |  | 201 | 120 |  |
| Males (%) | 52.0 | 67.5 | 0.004 | 41.8 | 67.5 | <0.0001 |
| Age (yrs) | 68 ± 7 | 66 ± 7 | 0.11 | 61 ± 8 | 64 ± 8 | <0.0001 |
| Age at Diabetes Dx (yrs) | 54 ± 9 | 53 ± 10 | 0.28 | 49 ± 10 | 49 ± 11 | 0.52 |
| Diabetes Duration (yrs) | 14 ± 7 | 13 ± 9 | 0.87 | 12 ± 8 | 14 ± 9 | 0.02 |
| BMI (Kg/m$^2$) | 30.0 ± 5 | 31.5 ± 7 | 0.04 | 30.9 ± 5 | 29.6 ± 5 | 0.38 |
| HbA1C (%) | 7.4 ± 1.1 | 7.5 ± 1.4 | 0.17 | 8.4 ± 1.8 | 8.6 ± 1.8 | 0.09 |
| Treatment |  |  |  |  |  |  |
| Diet Only (%) | 10.1 | 6.8 |  | 12.9 | 10.0 |  |
| Oral Agents (%) | 48.1 | 47.4 |  | 49.2 | 37.5 |  |
| Insulin (%) | 41.8 | 45.8 | 0.66 | 37.8 | 52.5 | 0.04 |
| Hypertension (%) | 68.4 | 79.7 | 0.10 | 75.1 | 84.0 | 0.04 |
| Ever Smoked (%) | 45.6 | 67.0 | 0.007 | 27.9 | 41.7 | 0.13 |

Each population included a group of cases with clinically significant CAD and a group of controls with negative cardiovascular history and a normal exercise treadmill test or angiography (Table 3). The overall prevalence of AAGIC carriers was similar in the two populations and not significantly different from that in non-diabetic individuals (0.538 in type 2 diabetic subjects from Boston, 0.551 in type 2 diabetic subjects from Italy, and 0.578 in non-diabetic subjects). Among the type 2 diabetic individuals from Boston, AAGIC carriers were significantly more frequent in CAD-positive cases than CAD-negative controls (OR=2.3, 95% CI 1.2-4.2, p=0.01 after adjusting for age, gender, and smoking) (Table 4). The risk of CAD associated with the carrier status for the AAGIC haplotype was estimated by logistic regression analysis using age, gender, and smoking as covariates. Potential differences in the association between genders or between studies were investigated by adding an interaction term (genotype*gender or genotype*study) to the model.

An association between AAGIC haplotype and CAD was also present in the Italian study, although the effect was smaller and did not reach statistical significance with this sample size (OR=1.4, 95% CI=0.9-2.3, p=0.14). The odds ratios were not significantly different between the two populations (p=0.34), and when the two studies were considered together, the common estimate of the CAD risk associated with the AAGIC haplotype was 1.6 (95% CI 1.1-2.3, p=0.015). In contrast with the findings for FFA, the increase in CAD risk associated with the AAGIC haplotype was similar in men and women (p=0.32 for interaction with gender). It was also independent of other cardiovascular risk factors such as hypertension and obesity. The relation to serum lipid traits could not be evaluated because of the high prevalence of antilipidemic treatment in these individuals.

TABLE 4

Risk of coronary artery disease associated with the CD36 AAGIC haplotype.

|  | Boston | | Italy | | Boston + Italy | |
| --- | --- | --- | --- | --- | --- | --- |
|  | CAD− | CAD+ | CAD− | CAD+ | CAD− | CAD+ |
| n | 79 | 118 | 201 | 120 | 280 | 238 |
| AAGIC Carriers (%) | 44.3 | 60.2 | 52.2 | 60.0 | 50.0 | 60.1 |
| Odds Ratio | 2.3† | | 1.4† | | 1.6‡ | |
| 95% CI | 1.2-4.2 | | 0.9-2.3 | | 1.1-2.3 | |
| p | 0.01 | | 0.14 | | 0.015 | |

†Adjusted for age, gender, and smoking.
‡Adjusted for age, gender, smoking, and population (Boston vs. Italy).

Example 4

Identification of Common Polymorphisms in the CD36 Locus

To identify common polymorphisms in functional regions that may be in linkage disequilibrium with the 'AAGIC' haplotype, we resequenced all exons together with 1.5 Kb of each promoter in 18 Caucasian individuals from the general population. One common sequence variant (−22674T>C) was detected that was not present in SNP databases (it was later designated RefSNP ID No. rs2151916). It was placed in the upstream promoter, 14 bases 5' of the transcription start site, in the core of a binding element for the transcriptional repressor GFI1B. This SNP was in complete linkage disequilibrium with the FFA-associated −33137A>G htSNP. This allele determines the presence of a binding site for the transcriptional repressor GFI1B (Tong et al., Mol. Cell. Biol., 18:2462-2473 (1998)), whereas allele C determines its absence. Thus, without wishing to be bound by theory, the presence of the T allele at −22674 may be a causative factor in the association between CD36 and cardiovascular risk.

No common variants affecting the coding sequence were identified. We also analyzed the relationship between the five htSNPs and an intron 3 microsatellite (in3TGn) that was previously found to be associated with the expression of an alternative spliced, inactive transcript and increased susceptibility to cerebral malaria in Thai (Daly et al., Nat. Genet., 29:229-32 (2001)). Two major alleles were found at this locus in our Caucasian population, corresponding to 12 and 13 TG repeats, with frequencies of 0.427 and 0.443, respectively. The 13 repeat allele (the one associated with the expression of the inactive transcript in Thai) corresponded almost exactly to the A allele at position −33137, whereas the 12 repeat allele was associated with the G allele. The 13-repeat allele may also be a causative factor.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining a human subject's risk of developing cardiovascular disease, the method comprising:
   providing a sample comprising genomic DNA from the subject; assaying the sample;
   detecting the presence, in one or both copies of a CD36 gene of the subject, one or both of:
      an "A" allele at polymorphism rs2366855, or
      an "A" allele at polymorphism rs1761667 and
   determining that the subject has an increased risk of developing cardiovascular disease.

2. The method of claim 1, wherein the assaying step comprises performing a procedure selected from the group consisting of: chain terminating sequencing, restriction digestion, allele-specific polymerase reaction, single-stranded conformational polymorphism analysis, genetic bit analysis, temperature gradient gel electrophoresis, ligase chain reaction, ligase/polymerase genetic bit analysis, allele specific hybridization, size analysis, nucleotide sequencing, 5' nuclease digestion, primer specific extension, and oligonucleotide ligation assay.

3. The method of claim 1, wherein the subject has a family history of cardiovascular disease.

4. The method of claim 1, wherein the cardiovascular disease is coronary artery disease (CAD).

5. The method of claim 1, wherein the cardiovascular disease is atherosclerosis.

6. The method of claim 1, wherein the detecting step comprises using a probe or primer that hybridizes under high stringency conditions to a nucleic acid sequence spanning the nucleotide.

7. The method of claim 1, further comprising determining whether the subject has, in one or both copies of the CD36 gene, an allele of a polymorphism associated with increased risk of developing cardiovascular disease selected from the group consisting of an "A" allele at rs1984112; a "G" allele at rs1527483; a deletion at rs3840546; and a "C" allele at rs1049673.

8. The method of claim 1, wherein the detecting step comprises detecting the presence in one or both copies of the CD36 gene in the subject, the following alleles of polymorphisms associated with increased risk of cardiovascular disease:
   an "A" allele at rs1984112;
   one or both of an "A" allele at rs2366855 or an "A" allele at rs1761667;
   a "G" allele at rs1527483;
   a deletion at rs3840546; and
   a "C" allele at rs1049673.

9. The method of claim 1, further comprising administering to the subject an agent to treat cardiovascular disease.

10. A method of determining a human subject's risk of developing cardiovascular disease, the method comprising:
    providing a sample comprising genomic DNA from the subject; and
    assaying the sample to detect the presence, in one or both copies of a CD36 gene of the subject, one or both of:
       an "A" allele at polymorphism rs2366855, or
       an "A" allele at polymorphism rs1761667; and
    based on the presence of an "A" allele at one or both of rs2366855 or rs1761667, determining that the subject has an increased risk of developing cardiovascular disease, wherein the subject has a family history of cardiovascular disease.

11. A method of determining a human subject's risk of developing cardiovascular disease, the method comprising:
    providing a sample comprising genomic DNA from the subject; and
    assaying the sample to detect the presence, in one or both copies of a CD36 gene of the subject, one or both of:
       an "A" allele at polymorphism rs2366855, or
       an "A" allele at polymorphism rs1761667; and
    based on the presence of an "A" allele at one or both of rs2366855 or rs1761667, determining that the subject has an increased risk of developing cardiovascular disease, wherein the assaying step comprises using a probe or primer that hybridizes under high stringency conditions to a nucleic acid sequence spanning the nucleotide.

12. A method of determining a human subject's risk of developing cardiovascular disease, the method comprising:
    providing a sample comprising genomic DNA from the subject; and assaying the sample to detect the presence, in one or both copies of a CD36 gene of the subject, one or both of:
  an "A" allele at polymorphism rs2366855, or
  an "A" allele at polymorphism rs1761667;
based on the presence of an "A" allele at one or both of rs2366855 or rs1761667, determining that the subject has an increased risk of developing cardiovascular disease; and,
administering to the subject an agent to treat cardiovascular disease.

* * * * *